(12) United States Patent
Takasaki

(10) Patent No.: US 8,670,028 B2
(45) Date of Patent: Mar. 11, 2014

(54) IMAGE PICKUP DEVICE AND ENDOSCOPE

(75) Inventor: Kosuke Takasaki, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 633 days.

(21) Appl. No.: 12/888,109

(22) Filed: Sep. 22, 2010

(65) Prior Publication Data
US 2011/0074941 A1    Mar. 31, 2011

(30) Foreign Application Priority Data
Sep. 25, 2009   (JP) .................. 2009-221165

(51) Int. Cl.
*A61B 1/04*   (2006.01)
*A61B 1/06*   (2006.01)

(52) U.S. Cl.
USPC .......................................... 348/68; 600/176

(58) Field of Classification Search
USPC ........ 348/68, 76, 373, 340; 600/176; 359/820
See application file for complete search history.

(56) References Cited

U.S. PATENT DOCUMENTS

| | | | |
|---|---|---|---|
| 4,677,471 A | 6/1987 | Takamura et al. | |
| 5,220,198 A | 6/1993 | Tsuji | |
| 5,894,369 A * | 4/1999 | Akiba et al. | 359/820 |
| 6,695,775 B2 * | 2/2004 | Watanabe et al. | 600/176 |
| 7,671,919 B2 * | 3/2010 | Iwasaki et al. | 348/373 |
| 7,692,710 B2 * | 4/2010 | Shimamura et al. | 348/340 |
| 2008/0239071 A1 * | 10/2008 | Takahashi | 348/76 |
| 2008/0316344 A1 | 12/2008 | Yamamiya | |

FOREIGN PATENT DOCUMENTS

| | | |
|---|---|---|
| FR | 2 782 735 A1 | 3/2000 |
| JP | 2000-147391 A | 5/2000 |
| JP | 2003-284686 A | 10/2003 |
| JP | 2007-260190 A | 10/2007 |

OTHER PUBLICATIONS

EP Communication, dated Apr. 20, 2011, issued in corresponding EP Application No. 10251607.7, 5 pages.

* cited by examiner

*Primary Examiner* — Gims Philippe
(74) *Attorney, Agent, or Firm* — Sughrue Mion, PLLC

(57) ABSTRACT

An image pickup device includes: an image pickup element; a spacer surrounding a light receiving surface of the image pickup element; a cover glass attached to the spacer, the cover glass being disposed opposing to the light receiving surface; and an insulative resin configured to thermally couple the image pickup element with the cover glass, and to have a thermal conductivity of not less than 8 W/mK. An endoscope includes: the image pickup device; an image pickup optical system; a drive circuit; a light guide configured to radiate light from a illumination light source; a tubular body configured to accommodate the image pickup device, the image pickup optical system, the drive circuit, the light guide, and a forceps opening; and a first insulative resin having a thermal conductivity of not less than 8 W/mK, and adapted to thermally couple the image pickup device with the drive circuit.

9 Claims, 10 Drawing Sheets

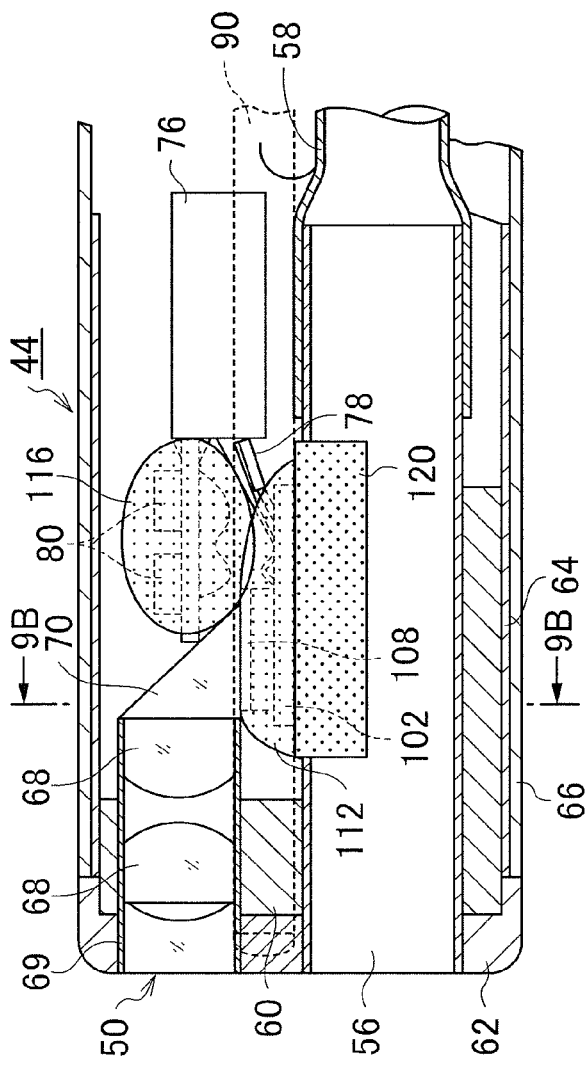
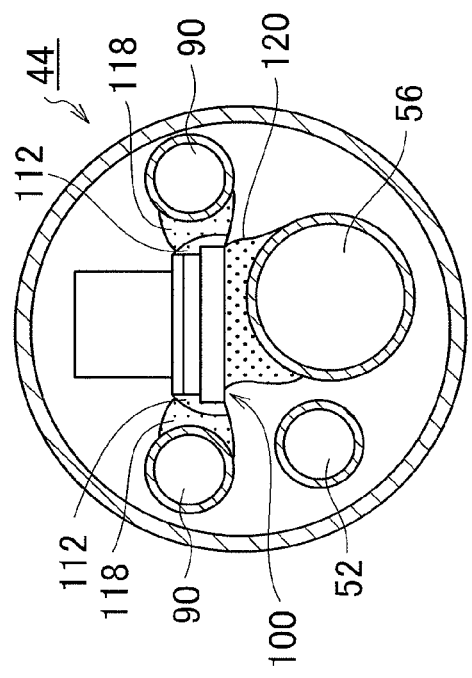
FIG.9A
FIG.9B

IMAGE PICKUP DEVICE AND ENDOSCOPE

BACKGROUND OF THE INVENTION

1. Field of the Invention

The presently disclosed subject matter relates to an image pickup device and an endoscope, and particularly to a technology to prevent dew condensation on a cover glass disposed on the image pickup plane side of an image pickup element.

2. Description of the Related Art

An endoscope includes an insertion part to be inserted into a body of a subject. At the distal end part of the insertion part, an observation optical system which is made up of lenses and prisms is provided. An image pickup device is disposed at an image formation position of the observation optical system. An observed image is taken by the image pickup device through a lens and is subjected to a photo-electric conversion. An electrical signal after photo-electric conversion is appropriately processed at a processor, and is thereafter outputted to a monitor/TV so that the observed image is displayed on the monitor/TV.

In general, an image pickup device includes a solid-state image pickup element and a cover glass spaced apart at a fixed distance (gap) from the solid-state image pickup element. This gap allows the elimination of the attenuation of light thereby improving the light condensing efficiency of a micro-lens layer of the solid-state image pickup element.

However, providing a gap may cause a problem of dew condensation. When a gap is formed in an image pickup device, water vapor may permeate into the gap to be absorbed into a micro-lens etc. (resin) of the solid-state image pickup element during cleaning and inspection of the endoscope. Then, upon operation of the solid-state image pickup element, it generates heat. Due to this heat generation, the moisture absorbed in the micro-lens etc. (resin) is released into the gap resulting in a dew condensation on the surface of the cover glass. Since the dew condensation is picked up as an observed image by the solid-state image pickup element, it may cause a degradation of the visibility thereof leading to a misdiagnosis.

Methods for preventing dew condensation within an image pickup device have been proposed. In Japanese Patent Application Laid-Open No. 2007-260190, an endoscope apparatus, in which a prism is optically connected with a solid-state image pickup element via a cover glass, is provided with a heater affixed to the rear surface of the prism. By actively providing heat to the cover glass through the heater, the temperature difference between the solid-state image pickup element and the cover glass is reduced thereby preventing dew condensation.

In Japanese Patent Application Laid-Open No. 2003-284686, an image pickup device for an endoscope in which a cover glass and a solid-state image pickup element are optically connected is provided with a peripheral circuit disposed adjacent to the cover glass. As the result of the cover glass receiving the heat generated from the peripheral circuit, the temperature difference between the outer and inner surfaces of the cover glass can be reduced even when the distal end of an insertion part is rapidly cooled. Thereby, dew condensation on the inner surface of the cover glass is prevented.

In Japanese Patent Application Laid-Open No. 2000-147391, an image pickup part of an endoscope is made up of a combination optical system, a solid-state image pickup element, and a partition wall for optically connecting the both. A gap is made up of the combination optical system, the solid-state image pickup element and the partition. A vent hole is provided in the partition wall so that the gap is in communication with the outer space. Thereby, the water vapor produced in the gap due to heat generation from the solid-state image pickup element is discharged to the outer space.

SUMMARY OF THE INVENTION

However, in the image pickup device of Japanese Patent Application Laid-Open No. 2007-260190, installing a heater will result in an increase in the number of parts, which will hinder the downsizing of the device. Further, since a micro wiring is needed for the heater, the ease of assembly will be reduced.

In the image pickup device of Japanese Patent Application Laid-Open No. 2003-284686, since the peripheral circuit is merely disposed adjacent to the cover glass, an effective transfer of the heat generated from the peripheral circuit to the cover glass is difficult.

The image pickup part of the endoscope of Japanese Patent Application Laid-Open No. 2000-147391 discharges water vapor in the gap into the outer space. However, the humidity of the outer space formed inside the endoscope is same as that of the gap, dew condensation in the gap cannot be prevented.

The presently disclosed subject matter has been made in view of such circumstances, and has an object to provide an image pickup device and an endoscope, which can prevent dew condensation.

In order to achieve the above described object, a first aspect of the presently disclosed subject matter provides an image pickup device including: an image pickup element; a spacer surrounding a light receiving surface of the image pickup element; a cover glass attached to the spacer, the cover glass being disposed opposing to the light receiving surface; and an insulative resin configured to thermally couple the image pickup element with the cover glass, the insulative resin having a thermal conductivity of not less than 8 W/mK.

According to the presently disclosed subject matter, the solid-state image pickup element and the cover glass are thermally coupled with an insulative resin having a high thermal conductivity. Even if the moisture absorbed into a resin such as a micro lens etc. on the solid-state image pickup element is converted into water vapor due to the heat generated during the operation of the solid-state image pickup element, the heat of the solid-state image pickup element is transferred to the cover glass via the insulative resin having a high thermal conductivity. As a result, since the temperature of heat generation of the solid-state image pickup element and the temperature of the cover glass can be approximately equalized, the occurrence of dew condensation on the inner surface of the cover glass can be prevented.

A second aspect of the presently disclosed subject matter provides an image pickup device according to the first aspect, wherein the insulative resin includes a diamond filler. By incorporating a diamond filler having a high thermal conductivity in the insulative resin, an insulative resin having a thermal conductivity of not less than 8 W/km can be obtained.

A third aspect of the presently disclosed subject matter provides an image pickup device according to the first or second aspect, further including: a frame of graphite sheet configured to accommodate the image pickup element, the cover glass, and the insulative resin, the frame of graphite sheet being thermally coupled with the insulative resin. Since the thermal conductivity of the graphite sheet is not less than 500 W/Km, it can transfer the heat generated from the solid-state image pickup element to the cover glass. The graphite sheet can be formed into a thin film of a thickness of about 100 μm. Therefore, it will not hinder the downsizing of the image pickup device. Moreover, since the graphite sheet is bendable, the graphite sheet can be easily processed into a predetermined shape. Thereby, it is possible to surround the solid-state image pickup element, the cover glass, and the insulative resin on three or more sides with the graphite sheet. A symmetrical disposition in a normal direction to the light receiving surface of the solid-state image pickup element can improve the balance of heat transfer. Therefore, surrounding the above described parts on three or four sides with the graphite sheet is preferable.

In order to achieve the above described object, a fourth aspect of the presently disclosed subject matter provides an endoscope including: the image pickup device according to any one of the first to third aspect; an image pickup optical system optically coupled with the image pickup device; a drive circuit electrically connected with the image pickup device; a light guide configured to radiate light from a illumination light source; a forceps opening; a tubular body configured to accommodate the image pickup device, the image pickup optical system, the drive circuit, the light guide, and the forceps opening; and a first insulative resin having a thermal conductivity of not less than 8 W/mK, the first insulative resin being adapted to thermally couple the image pickup device with the drive circuit.

According to the presently disclosed subject matter, since the heat generated from the drive circuit can be transferred to the cover glass, the temperature difference between the solid-state image pickup element and the cover glass can be effectively reduced.

A fifth aspect of the presently disclosed subject matter provides an endoscope according to the fourth aspect, further including: a second insulative resin having a thermal conductivity of not less than 8 W/mK, the second insulative resin being adapted to thermally couple the image pickup device with the light guide.

Transferring the heat from the light guide, which generates a larger amount of heat, to the image pickup device allows the temperature difference between the solid-state image pickup element and the cover glass to be more effectively reduced. Moreover, by transferring the heat generated at the light guide to the image pickup device, a temperature increase of the light guide can be prevented. This will make it possible to avoid the problem that the temperature of the distal end of the endoscope becomes high and thus not usable for the sake of safety.

A sixth aspect of the presently disclosed subject matter provides an endoscope according to the fourth or fifth aspect, wherein the frame of the graphite sheet accommodates the drive circuit and the first insulative resin. The heat generated from the drive circuit can be effectively transferred to the image pickup device.

A seventh aspect of the presently disclosed subject matter provides an endoscope according to the fourth aspect, wherein the insulative resin and the first insulative resin have a same composition. By arranging that the insulative resin and the first insulative resin are the same resin, the insulative resin and the first insulative resin can be integrally produced. This will make the assembly of the endoscope easy.

An eighth aspect of the presently disclosed subject matter provides an endoscope according to the fifth aspect, wherein the first insulative resin and the second insulative resin have a same composition.

A ninth aspect of the presently disclosed subject matter provides an endoscope according to the fifth aspect, wherein the insulative resin, the first insulative resin and the second insulative resin have a same composition. By arranging that the insulative resin, the first insulative resin, and the second insulative resin are the same resin, the insulative resin, the first insulative resin, and the second insulative resin can be integrally manufactured. This will make the assembly of the endoscope easy.

A tenth aspect of the presently disclosed subject matter provides an endoscope according to the fifth aspect, further including: a heat release member configured to thermally couple the forceps opening with any one of the insulative resin, the first insulative resin, and the second insulative resin. By transferring the heat accumulated in the insulative resin, the first insulative resin, and the second insulative resin to the forceps opening via the heat release member, it is possible to suppress temperature increase of the endoscope.

According to the presently disclosed subject matter, an image pickup device and an endoscope, which are compact and highly sensitive, and can prevent dew condensation are provided.

BRIEF DESCRIPTION OF THE DRAWINGS

FIGS. 9A and 9B are sectional views of the distal end part of an endoscope insertion part in which an image pickup device is incorporated.

DETAILED DESCRIPTION OF THE PREFERRED EMBODIMENTS

Hereafter, preferred embodiments of the presently disclosed subject matter will be described according to appended drawings. Although the presently disclosed subject matter will be described by the following preferred embodiments, modifications can be made in many ways without departing from the scope of the presently disclosed subject matter, and other embodiments other than the present embodiment can be utilized. Therefore, all the modifications within the scope of the invention will be included in the claims. Moreover, a numerical range herein represented by using "to" means that the range includes numerical values described before and after "to".

Figure 1:
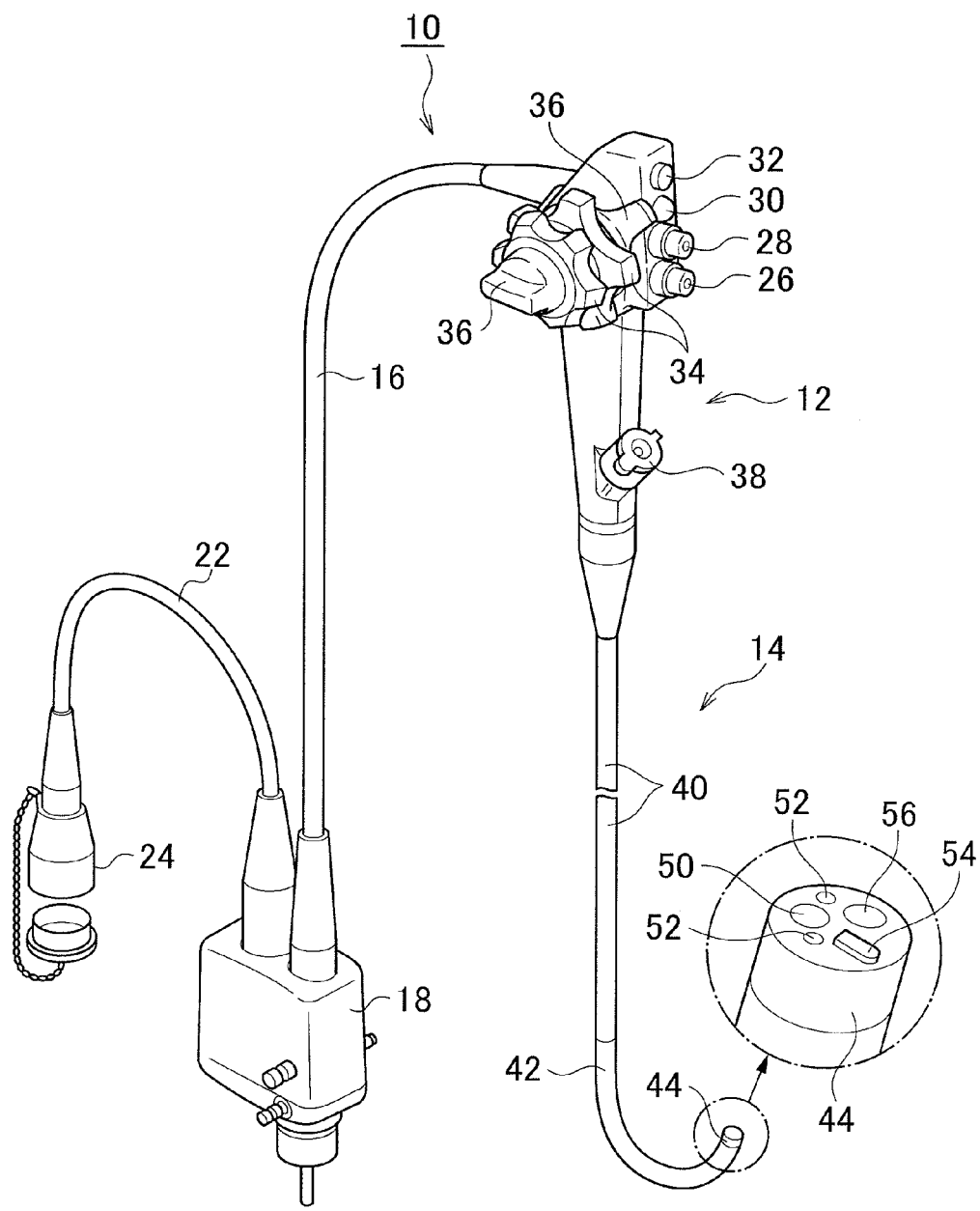
FIG. 1 is a perspective view of an endoscope relating to an embodiment of the presently disclosed subject matter.

FIG. 1 is a perspective view to illustrate an endoscope of the present embodiment. As illustrated in FIG. 1, an endoscope 10 includes a proximal operation part 12, and an insertion part 14 which is linked to the proximal operation part 12. The proximal operation part 12 is grasped by an operator, and the insertion part 14 is inserted into the body of a subject.

A universal cable 16 is connected to the proximal operation part 12, and an LG connector 18 is provided at a tip end of the universal cable 16. The LG connector 18 is detachably linked to a light source apparatus not illustrated so that illumination light is fed to an illumination optical system 52 arranged in the distal end part of the insertion part 14. Moreover, an electric connector 24 is connected to the LG connector 18 via a cable 22, and the electric connector 24 is detachably linked to a processor which is not illustrated. Thereby, the data of the observed image acquired by the endoscope 10 is outputted to the processor, and further an image is displayed on a monitor (not illustrated) connected to the processor.

Moreover, air feed/water feed button 26, a suction button 28, a shutter button 30, and a function switching button 32 are provided adjacent to each other in the proximal operation part 12. The air feed/water feed button 26 is an operation button for ejecting air or water toward the observation optical system 50 from an air feed/water feed nozzle 54 disposed in the distal end part 44 of the insertion part 14. The suction button 28 is an operation button for drawing a lesion, etc. from the forceps opening 56 disposed in the distal end part 44. The shutter button 30 is an operation button for controlling the recording of observed images, and the like. The function switching button 32 is an operation button for switching the functions of the shutter button 30, and others.

Moreover, in the proximal operation part 12, a pair of angling knobs 34, 34 and a pair of locking levers 36, 36 are provided. By operating the angling knob 34, the bending operation of a bending part 42 described later is performed, and by operating the locking lever 36, the locking and unlocking of the angling knob 34 is performed.

Further, the proximal operation part 12 is provided with a forceps insertion part 38, and the forceps insertion part 38 is configured to be in communication with a forceps opening 56 of the distal end part 44. Therefore, by inserting an endoscope treatment tool such as forceps (not illustrated) from the forceps insertion part 38, the endoscope treatment tool can be drawn out from the forceps opening 56.

On the other hand, the insertion part 14 is made up of a soft part 40, a bending part 42, and a distal end part 44 in this order from the side of the proximal operation part 12. The soft part 40 is flexible and is made up by coating a core member, which is made from a metal mesh tube or a helix tube of metal plate, with resin, etc.

The bending part 42 is configured so as to be remotely bent by rotating the angling knob 34, 34 of the proximity operation part 12. For example, the bending part 42 is configured such that a plurality of tubular node rings (not illustrated) are rotatably linked by a guide pin (not illustrated) and a plurality of operation wires are inserted through the node rings and are guided by the guide pin. The operation wire is inserted through the soft part 40 of the insertion part 14 in a state of being inserted through a contact coil, and is linked to the angling knob 34, 34 of the proximity operation part 12 via a pulley (not illustrated) etc. By this configuration, the angling knob 34, 34 is operated to pull or push the operation wire so that the node rings (not illustrated) are rotated and bending operation of the bending part 42 is performed.

In the distal end surface (the side surface in the case of a side endoscope) of the distal end part 44 is provided with an observation optical system (observation lens) 50, an illumination optical system (illumination lens) 52, an air feed/water feed nozzle 54, a forceps opening 56, and others.

The light guide 52 is provided adjacent to the observation optical system 50 and can be disposed on both sides of the observation optical system 50 as needed. The light guide 52 is inserted through the insertion part 14, the proximal operation part 12, and a universal cable 16, and the incoming end of the light guide is disposed in an LG connector 18. Therefore, by linking the LG connector 18 with a light source apparatus (not illustrated), the illumination light radiated from the light source apparatus is transmitted to the light guide 52, thereby being radiated from the light guide 52 to an observation range ahead.

The air feed/water feed nozzle 54 is opened toward the observation optical system 50, and an air feed/water feed tube (not illustrated) is connected to the air feed/water feed nozzle 54. The air feed/water feed tube is inserted through the insertion part 14 and is branched at some middle point thereafter being connected to an air feed/water feed valve (not illustrated) in the proximal operation part 12. The air feed/water feed valve is operated with an air feed/water feed button 26 so that air or water is sprayed from the air feed/water feed nozzle 54 toward the observation optical system 50.

A tubular forceps channel 58 (see FIG. 4) is connected to the forceps opening 56, and the forceps channel 58 is inserted through the inside of the insertion part 14. The forceps channel 58 is branched and thereafter one of it is communicated with a forceps insertion part 38 in the proximal operation part 12 and the other is connected to a suction valve (not illustrated) in the proximal operation part 12. The suction valve is operated with a suction button 28, and is thereby able to suck a lesion etc. from the forceps opening 56. It is noted that the forceps opening 56 and the forceps channel 58, etc. are to be provided as needed, and they may be omitted for example in the case of an intranasal endoscope.

Figure 2:
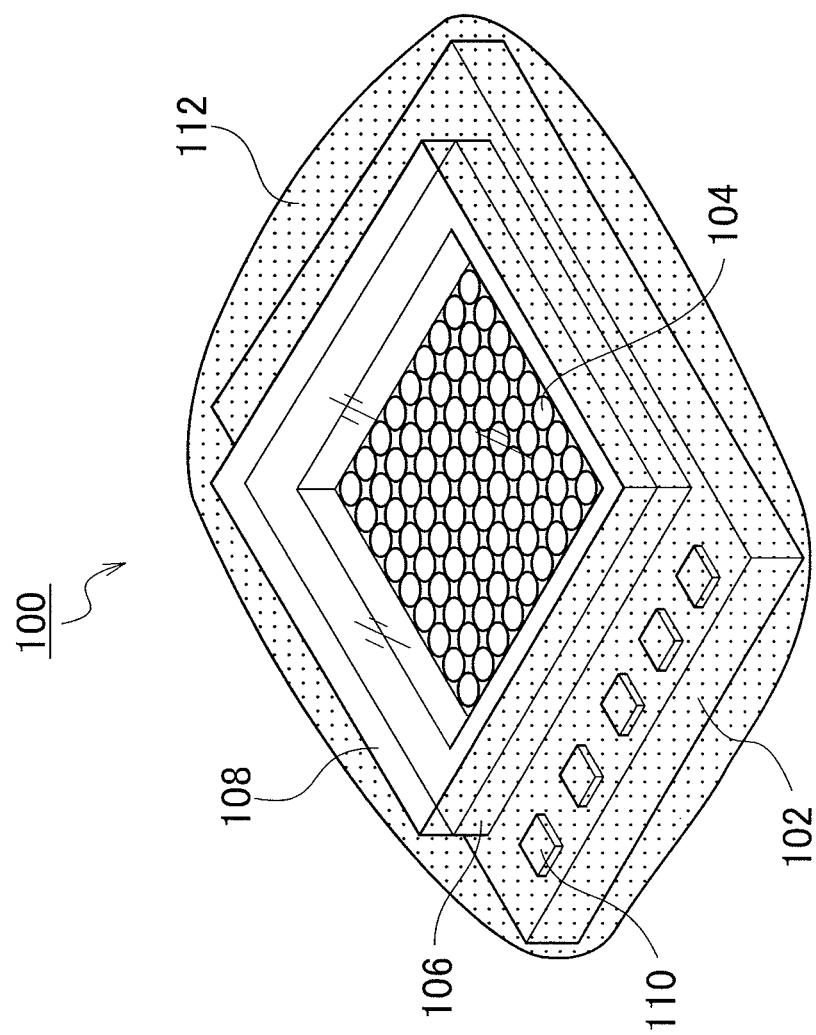
FIG. 2 illustrates the configuration of an image pickup device relating to an embodiment of the presently disclosed subject matter.

FIG. 2 is a perspective view illustrating the appearance profile of an image pickup device relating to an embodiment of the presently disclosed subject matter. The image pickup device 100 includes a solid-state image pickup element 102, a spacer 106 of a frame shape surrounding the light receiving surface 104 of the solid-state image pickup element 102, a cover glass 108 attached to the spacer 106, a pad 110 provided on the solid-state image pickup element 102. The image pickup device 100 includes a gap formed of the light receiving surface 104, the spacer 106, and the cover glass 108. The gap allows the attenuation of light to be eliminated. Moreover, it can improve the light condensing efficiency of a micro lens layer (not illustrated) which is formed on the light receiving surface 104 of the solid-state image pickup element 102. That is, a compact and highly sensitive image pickup device can be obtained.

An insulative resin 112 covers the side surfaces of the solid-state image pickup element 102 and the cover glass 108 excluding the top surface of the cover glass 108, and thermally couples the solid-state image pickup element 102 with the cover glass 108. The insulative resin 112 has a thermal conductivity of not less than 8 W/mK. The insulative resin 112 can be obtained, for example, by incorporating a diamond filler in a silicone, epoxy or urethane resin having insulation properties. By covering the solid-state image pickup element 102 and the cover glass 108 with the insulative resin 112 having a high thermal conductivity, it is possible to transfer the heat generated when the solid-state image pickup element 102 is driven to the cover glass 108. Thus, the temperature difference between the solid-state image pickup element 102 and the cover glass 108 is decreased thereby allowing the prevention of dew condensation on the inner surface of the cover glass 108.

In the embodiment of FIG. 2, four side surfaces excluding the top surface of the cover glass 108 are covered with the insulative resin 112. Without being limited to this embodiment, the range of coating with the insulative resin 112 will not be limited provided that the temperature difference between the solid-state image pickup element 102 and the cover glass 108 can be reduced. In order to reduce the temperature difference between the solid-state image pickup element 102 and the cover glass 108, the range of coating with the insulative resin 112 is appropriately determined from the thermal conductivity of the insulative resin 112 and the amount of heat generated by the solid-state image pickup element 102.

Figure 3:
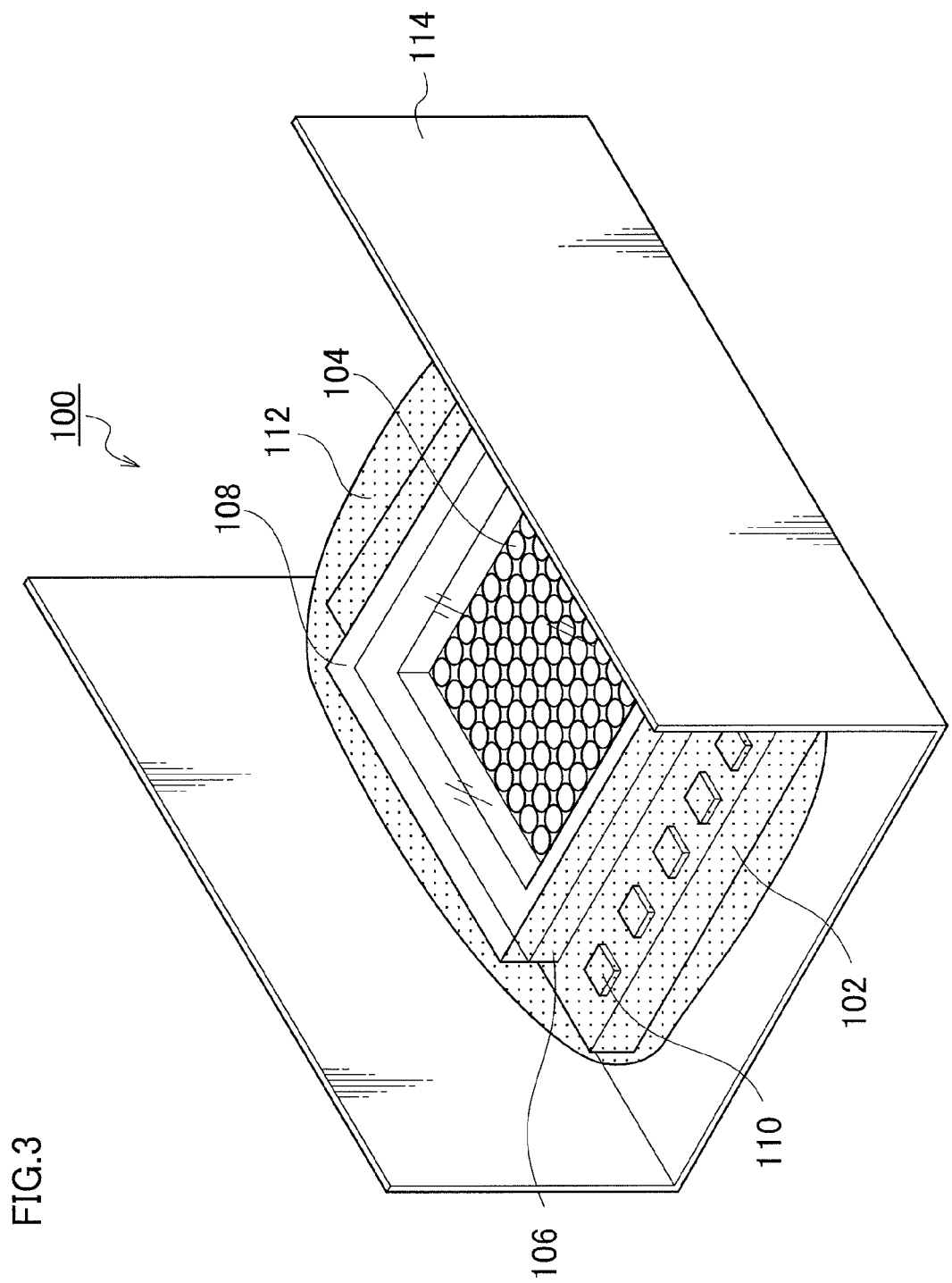
FIG. 3 illustrates the configuration of an image pickup device relating to another embodiment of the presently disclosed subject matter.

FIG. 3 is a perspective view illustrating the appearance profile of an image pickup device relating to another embodiment of the presently disclosed subject matter. The same configurations as those of the embodiment of FIG. 2 may be designated by the same reference numerals thereby omitting the description thereof. The image pickup device 100 includes a solid-state image pickup element 102, a spacer 106 of a frame shape surrounding a light receiving surface 104 of the solid-state image pickup element 102, a cover glass 108 attached to the spacer 106, a pad 110 provided on the solid-state image pickup element 102, and an insulative resin 112 to coat the solid-state image pickup element 102 and the cover glass 108.

The image pickup device 100 further includes a frame 114 which is made from a graphite sheet which accommodates the solid-state image pickup element 102, the cover glass 108, and the insulative resin 112. The frame 114 has a thickness of 30 to 100 μm and can be folded freely. The thermal conductivity of the frame 114 is not less than 500 W/mK.

Thermally coupling the frame 114 with the insulative resin 112 allows the heat generated from the solid-state image pickup element 102 to be effectively transferred to the cover glass 108. The frame 114 can be used as a mold when coating the solid-state image pickup element 102 and the cover glass 108 with the insulative resin 112. First, the frame 114 having three surfaces is prepared. Next, the image pickup device 100 is disposed within the space formed in the frame 114. Lastly, by pouring the insulative resin 112 thereinto, it is possible to easily coat the solid-state image pickup element 102 and the cover glass 108 with the insulative resin 112.

Figure 4:
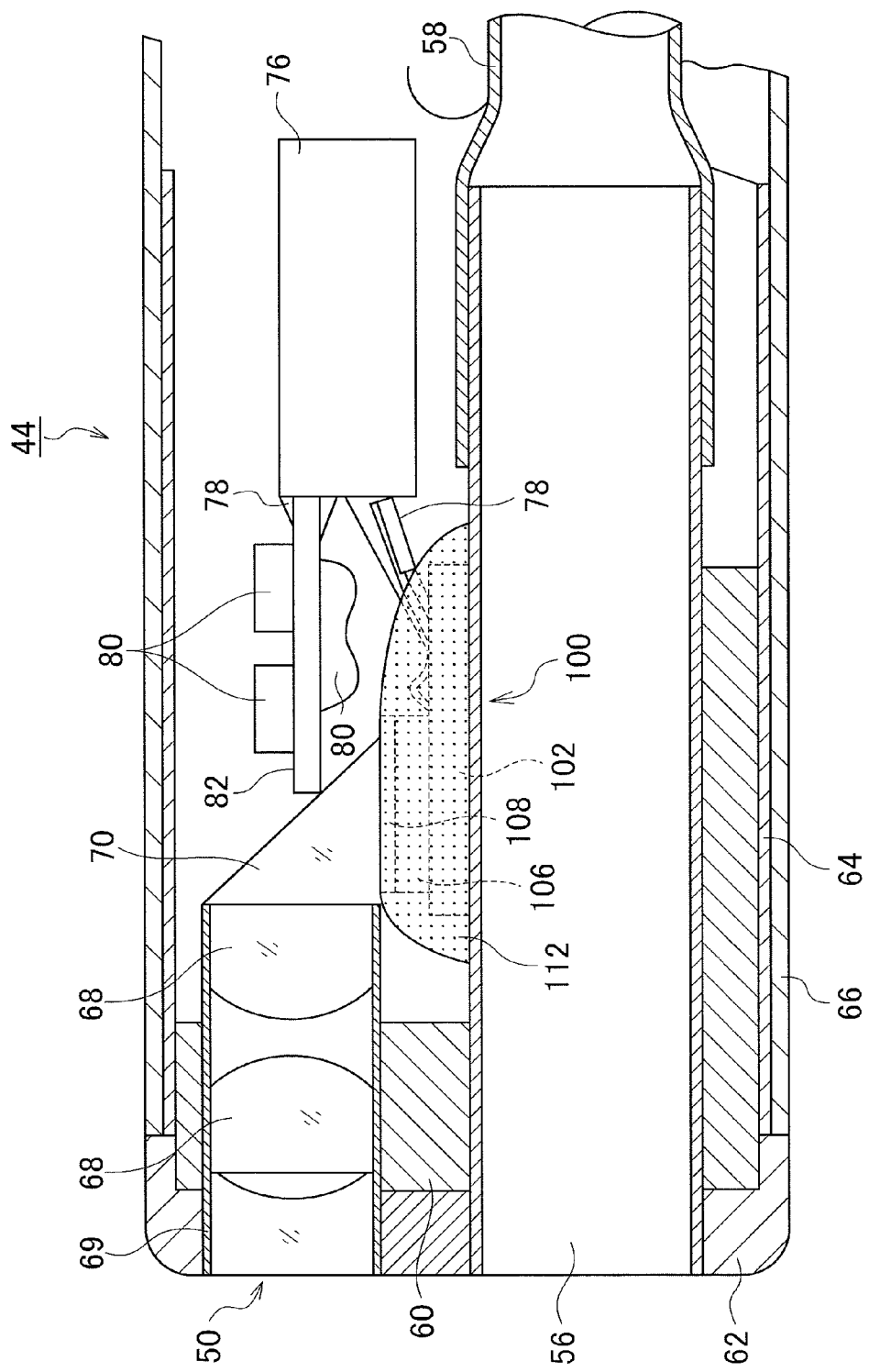
FIG. 4 is a sectional view of the distal end part of an endoscope insertion part in which an image pickup device is incorporated.

FIG. 4 illustrates a section of a distal end part 44 of the insertion part relating to an embodiment of the presently disclosed subject matter. As illustrated in FIG. 4, an image pickup device 100 is disposed in the distal end part 44. The observation optical system 50 includes a lens 68, a lens barrel 69, and a prism 70 and is fixed in a state being inserted through a main body 60. The main body 60 is formed of metal etc. into a substantially cylindrical shape. A cap 62 made of resin is attached to the distal end side of the main body 60. Moreover, a distal end sleeve 64 of the bending part is outwardly fitted to the main body 60, and the periphery of the main body 60 is covered with a coating member 66.

An image pickup device 100 is attached to the prism 70 of the observation optical system 50. The image pickup device 100 includes a solid-state image pickup element 102, a spacer 106 of a frame shape surrounding the light receiving surface 104 of the solid-state image pickup element 102, a cover glass 108 attached to the spacer 106, and an insulative resin 112 to coat the solid-state image pickup element 102 and the cover glass 108. A pad (not illustrated) of the solid-state image pickup element 102 and a plurality of signal lines 78 in a cable 76 are electrically connected. The signal lines 78 are inserted through an insertion part, a universal cable, and the like as a multi-core cable, and extend to an electric connector to be connected to a processor (not illustrated). Therefore, an observed image captured at the observation optical system 50 is formed into an image on the light receiving surface of the solid-state image pickup element 102 and converted into an electric signal, and thereafter the signal is outputted to the processor through the signal line 78 to be converted into a video signal. Thus, an observed image is displayed on a monitor connected to the processor.

The insulative resin 112 is, for example, a silicone, epoxy or urethane resin which has insulating properties and is incorporated with a diamond filler by 50% as described above.

A circuit board 82 on which a peripheral circuit 80 is implemented is disposed in the vicinity of the prism 70. The circuit board 82 and the signal line 78 are electrically connected. The peripheral circuit 80 may be a circuit for processing the output signal from the solid-state image pickup element 102, or a circuit for driving the solid-state image pickup element 102. The function of the peripheral circuit 80 will not be limited.

In the endoscope configured as described above, the power supply of each device is turned on to observe the inside of the body cavity. An observed image captured by the observation optical system 50 while the inside of the body cavity is illuminated with the illumination light from the light guide is formed into an image on the light receiving surface of the solid-state image pickup element 102 to be converted into an electrical signal. The signal is outputted to the processor via the signal line 78 and is converted into a video signal. As a result of this, an observed image is displayed on a monitor connected to the processor. The solid-state image pickup element 102 is driven and heat is generated from the solid-state image pickup element 102. This heat causes the water in the gap to evaporate. In the presently disclosed subject matter, the heat generated from the solid-state image pickup element 102 is transferred to the cover glass 108 through the insulative resin 112 having a high thermal conductivity. As a result, the temperature difference between the solid-state image pickup element 102 and the cover glass 108 is reduced thereby preventing dew condensation within a gap.

Figure 5:
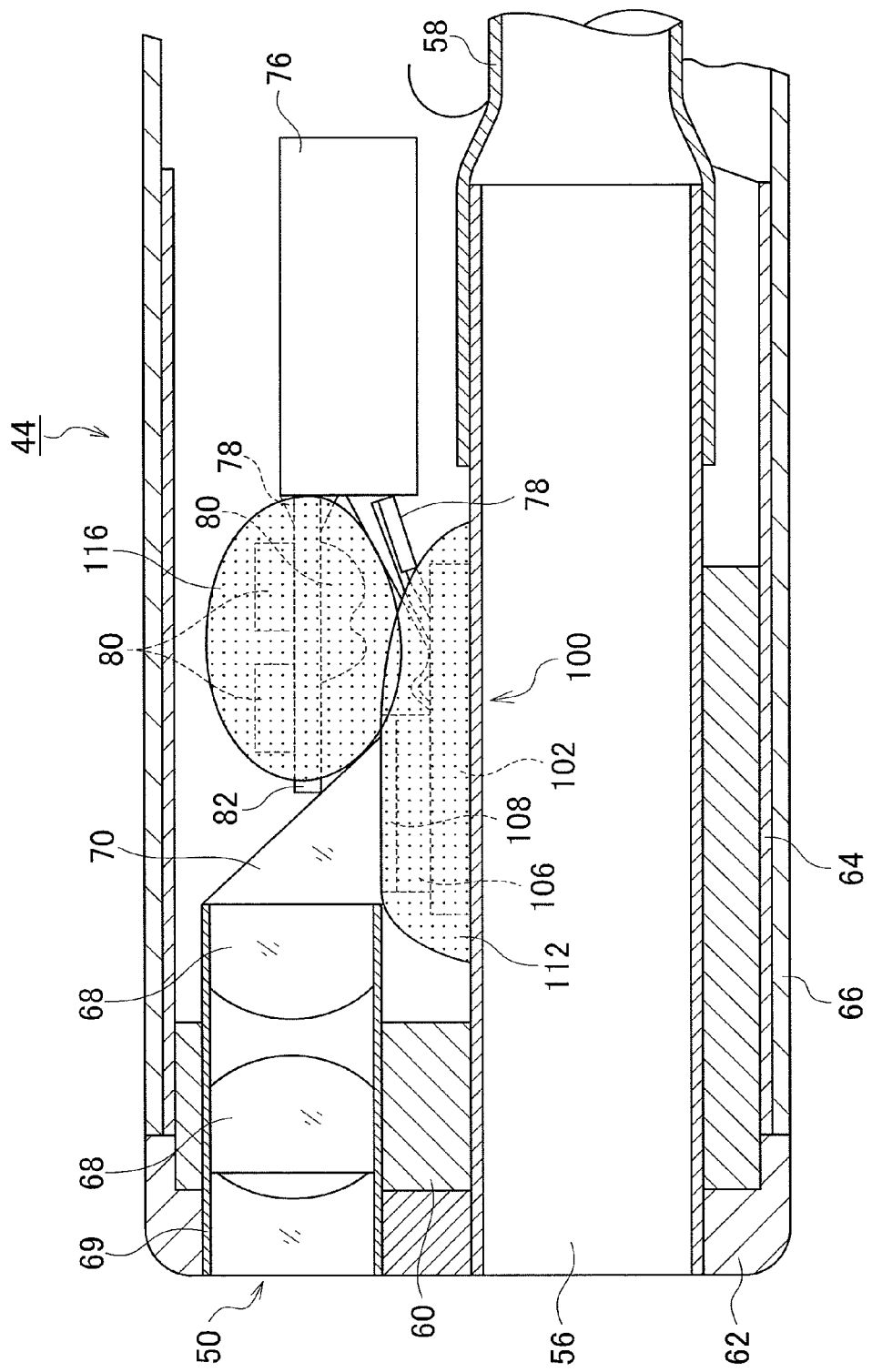
FIG. 5 is a sectional view of the distal end part of an endoscope insertion part in which an image pickup device is incorporated.

FIG. 5 illustrates a section of a distal end part 44 of an insertion part relating to a further embodiment of the presently disclosed subject matter. The configurations which are the same as those of the embodiment of FIG. 2 may be designated by the same reference numerals thereby omitting the description thereof. As illustrated in FIG. 5, the endoscope includes a first insulative resin 116 for coating the peripheral circuit 80 and the circuit board 82. The first insulative resin 116 is thermally coupled with insulative resin 112. The first insulative resin 116 preferably has a thermal conductivity of not less than 8 W/mK. The first insulative resin 116 is for example a silicon resin, epoxy resin or urethane resin which has insulating properties and is incorporated with a diamond filler. By coating the peripheral circuit 80 and the circuit board 82 with the first insulative resin 116 having a high thermal conductivity, it is possible to effectively transfer the heat generated at the peripheral circuit 80 to the image pickup device 100.

In the endoscope configured as described above, a power supply of each device is turned on to observe the inside of the body cavity. The peripheral circuit 80 and the solid-state image pickup element 102 are applied with a signal and are driven. This will cause the peripheral circuit 80 and the solid-state image pickup element 102 to generate heat. The heat generated from the both is transferred to the insulative resin 112 and the first insulative resin 116. In the present embodiment, in addition to the heat from the solid-state image pickup element 102, the heat from the peripheral circuit 80 is also transferred to the cover glass 108. Therefore, the temperature difference between the solid-state image pickup element 102 and the cover glass 108 can be reduced in a short period of time. Thermally coupling the insulative resin 112 with the first insulative resin 116 allows the dispersion of the heat from the solid-state image pickup element 102 and the peripheral circuit 80. Thus, it is possible to prevent heat from concentrating on the solid-state image pickup element 102 and the peripheral circuit 80.

The insulative resin 112 and the first insulative resin 116 may be resins having different compositions provided that they have high thermal conductivities. By arranging that the insulative resin 112 and the first insulative resin 116 have the same composition, the insulative resin 112 and the first insulative resin 116 can be integrally formed. Thus, it is possible to make the assembly of the endoscope easy at the time of the manufacturing thereof.

Figure 6:
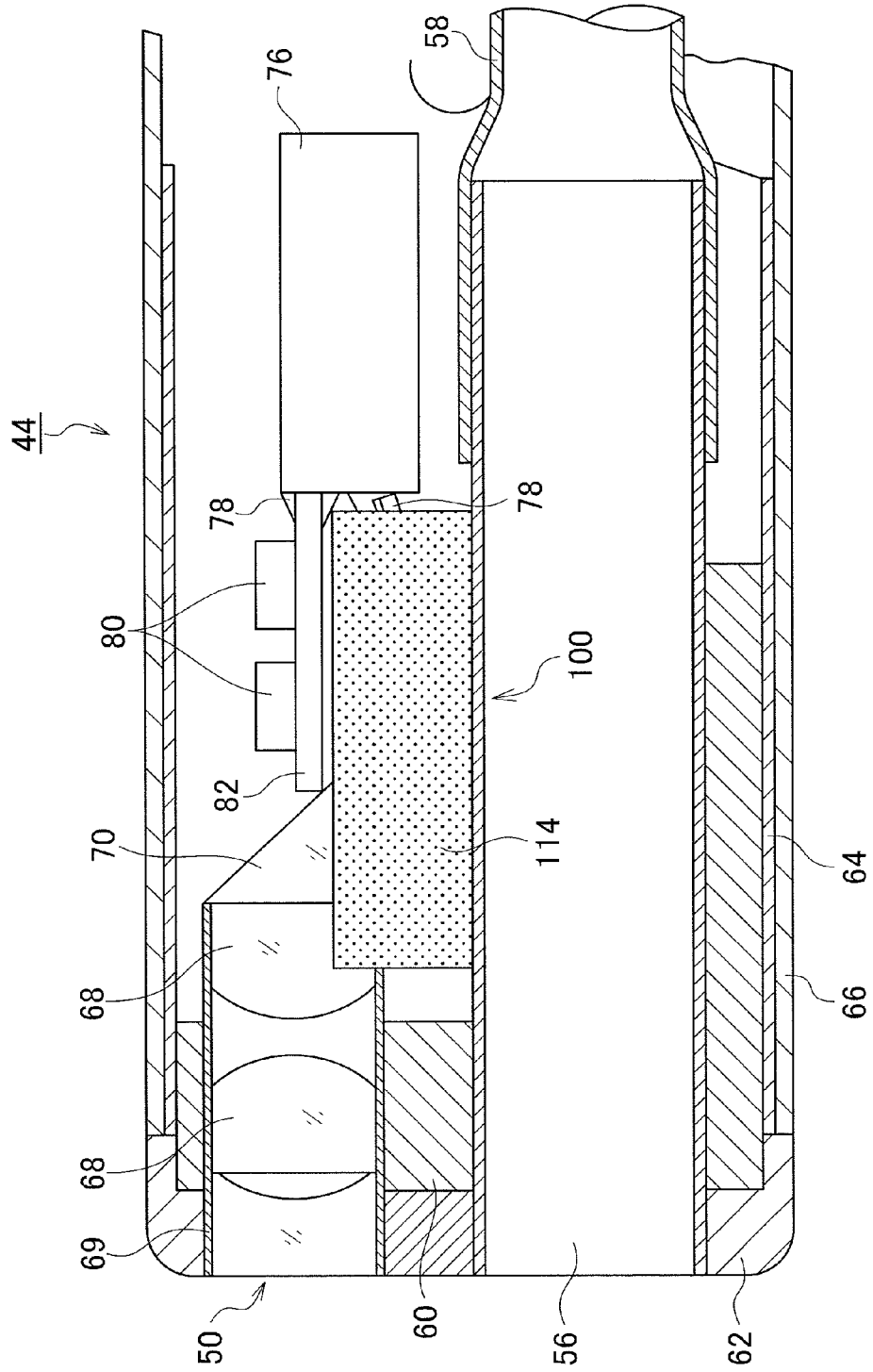
FIG. 6 is a sectional view of the distal end part of an endoscope insertion part in which an image pickup device is incorporated.

FIG. 6 illustrates a section of a distal end part 44 of an insertion part relating to a further embodiment of the presently disclosed subject matter. The configurations which are the same as those of the embodiment of FIG. 2 may be designated by the same reference numerals thereby omitting the description thereof. As illustrated in FIG. 6, a frame 114 made up of a graphite sheet is provided. The frame 114 surrounds the periphery of the image pickup device 100 on three or more sides. The frame 114 has a thermal conductivity of not less than 500 W/mK. The thermal conductivity of the frame 114 is larger than that of the insulative resin 112. Therefore, it is possible to efficiently transfer the heat generated at the solid-state image pickup element 102 to the cover glass 108. Moreover, the frame 114 has a function as a mold when coating the solid-state image pickup element 102 and the cover glass 108 with the insulative resin 112. Therefore, it is possible to easily coat the solid-state image pickup element 102 and the cover glass 108 with the insulative resin 112.

Figure 7:
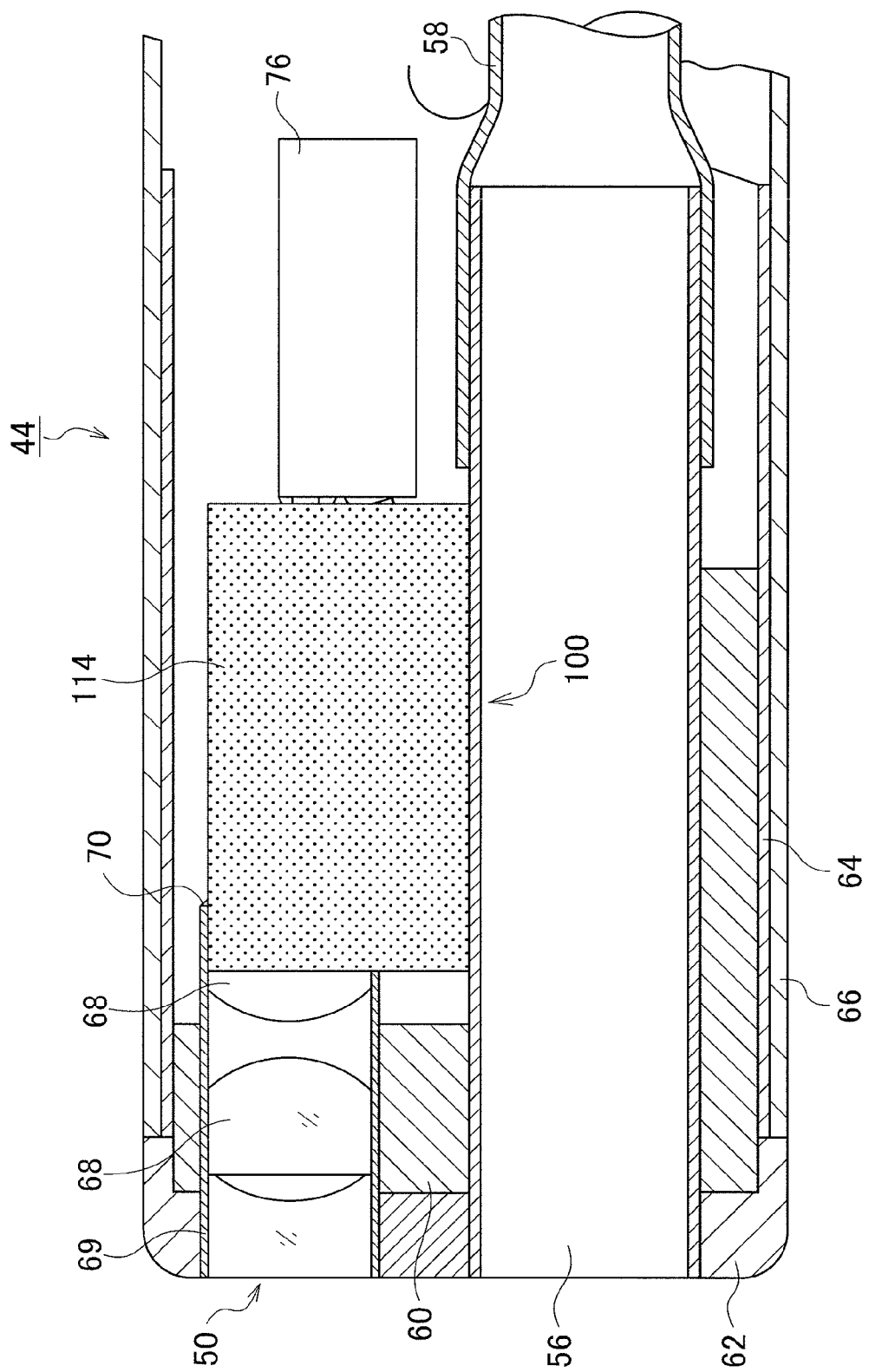
FIG. 7 is a sectional view of the distal end part of an endoscope insertion part in which an image pickup device is incorporated.

FIG. 7 illustrates a section of a distal end part 44 of an insertion part relating to a further embodiment of the presently disclosed subject matter. The configurations which are the same as those of the embodiment of FIG. 5 may be designated by the same reference numerals thereby omitting the description thereof. As illustrated in FIG. 7, a frame 114 made up of a graphite sheet is provided. The frame 114 surrounds the periphery of the image pickup device 100 and the circuit board 82 on which the peripheral circuit 80 is implemented, on three or more planes. The frame 114 has a thermal conductivity of not less than 500 W/mK. The thermal conductivity of the frame 114 is larger than that of the insulative resin 112. Therefore, it is possible to effectively transfer the heat generated at the solid-state image pickup element 102 to the cover glass 108. Moreover, the frame 114 has a function as a mold when coating the circuit board 82, on which the solid-state image pickup element 102, the cover glass 108, and the peripheral circuit 80 are implemented, with the insulative resin 112 and the first insulative resin 116. Therefore, the application of the insulative resin 112 and the first insulative resin 116 is easy.

Figures 8A, 8B:
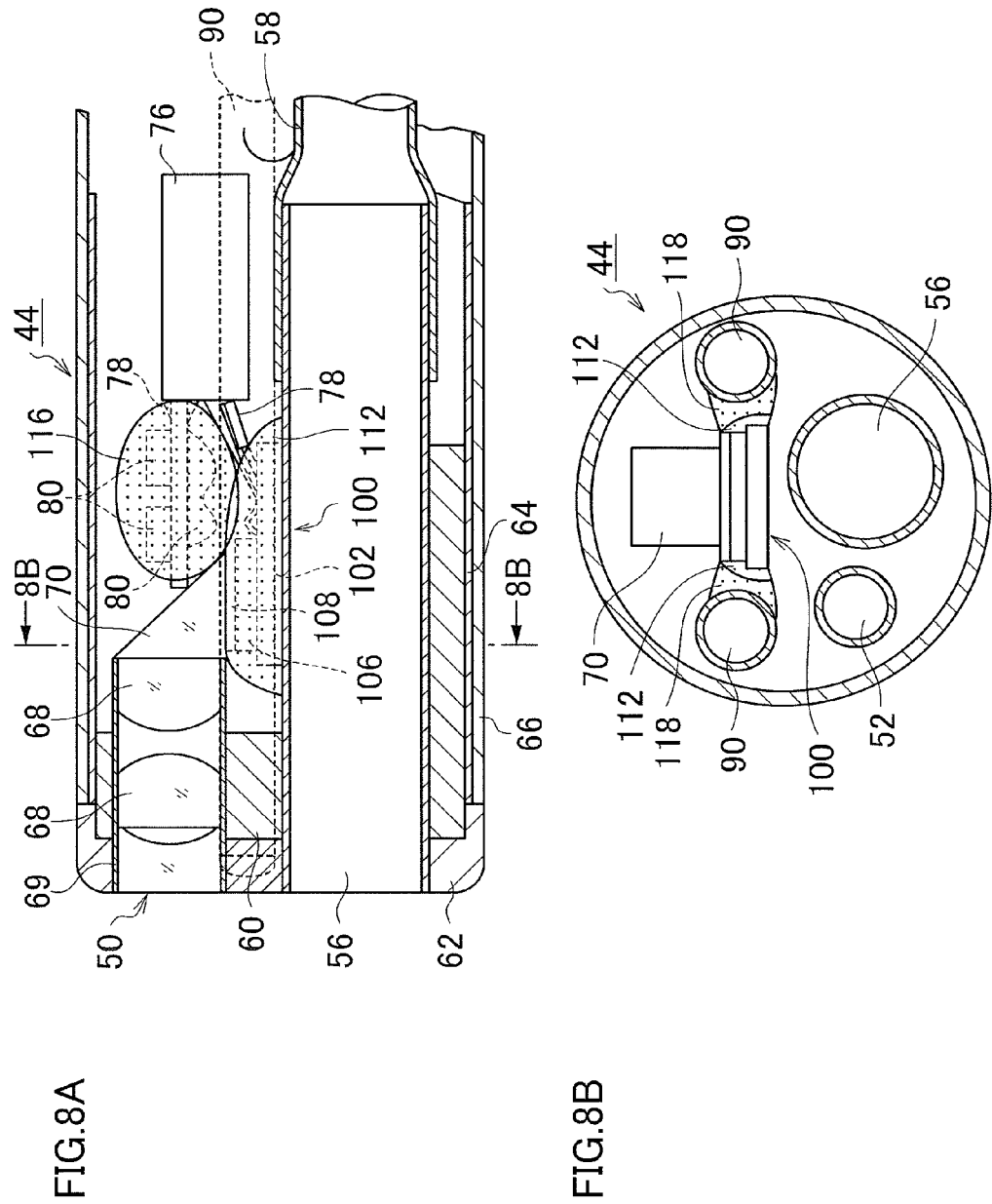
FIGS. 8A and 8B are sectional views of the distal end part of an endoscope insertion part in which an image pickup device is incorporated.

FIG. 8A illustrates a section of a distal end part 44 of an insertion part relating to a further embodiment of the presently disclosed subject matter. FIG. 8B is a sectional view based on the line 8B-8B. The configurations which are the same as those of the embodiment of FIG. 5 may be designated by the same reference numerals thereby omitting the description thereof. As illustrated in FIGS. 8A and 8B, the endoscope includes a second insulative resin 118 which thermally couples the light guide 90 with the image pickup device 100. The second insulative resin 118 preferably has a thermal conductivity of not less than 8 W/mK. The second insulative resin 118 is, for example, a resin made up of a silicone, epoxy or urethane resin which has insulating properties and is incorporated with a diamond filler.

The second insulative resin 118 may be a resin of a different composition from those of the insulative resin 112 and the first insulative resin 116 provided that it has a high thermal conductivity. By configuring the insulative resin 112, the first insulative resin 116 and the second insulative resin 118 to be a resin of the same composition, it is possible to integrally form the insulative resin 112, the first insulative resin 116 and the second insulative resin 118. Thereby, the assembly when manufacturing an endoscope can be made easy.

The light guide 90 radiates the light from the illumination light source to an affected part. The light guide 90 includes, for example, an optical fiber and a fluorophore which converts the wavelength of the light from the optical fiber. When light is radiated from the light guide 90, heat is generated at the distal end part thereof. The heat generated at the distal end part is transferred to the image pickup device 100 via the second insulative resin 118. Since, in this way, in addition to the heat from the solid-state image pickup element 102, the heat from the light guide 90 is also transferred, the temperature difference between the solid-state image pickup element 102 and the cover glass 108 can be reduced in a short period of time.

Moreover, the heats generated from the light guide 90, the solid-state image pickup element 102, and the peripheral circuit 80 are dispersed by the insulative resin 112, the first insulative resin 116, and the second insulative resin 118. Thus, the distribution of heat is made uniform and thereby a concentration of heat at one point can be avoided. Therefore, it is possible to avoid the problem that as the result of the heat generated at the distal end part being transferred to the image pickup device 100, which is located inside the endoscope, the temperature of the distal end part of the endoscope becomes high and thereby unusable for the sake of safety.

FIG. 9A illustrates a section of a distal end part 44 of an insertion part relating to a further embodiment of the presently disclosed subject matter. FIG. 9B is a sectional view based on the line 9B-9B. The configurations which are the same as those of the embodiment of FIG. 8 may be designated by the same reference numerals thereby omitting the description thereof. As illustrated in FIGS. 9A and 9B, the endoscope includes a heat release member 120 which thermally couples the insulative resin 112 with the forceps opening 56. By thermally coupling the forceps opening with at least one of the insulative resin 112, the first insulative resin 116, and the second insulative resin 118 with the heat release member, the occurrence of dew condensation inside the cover glass 108 is inhibited and the heats generated at the solid-state image pickup element 102, the peripheral circuit 80, and the light guide 90 can be effectively discharged to the outside. The heat release member 120 may be of any material having a high thermal conductivity, and a resin made up of a silicone, epoxy or urethane resin which has insulating properties and is incorporated with a diamond filler, or a graphite sheet can be used.

Figures 10A, 10B:
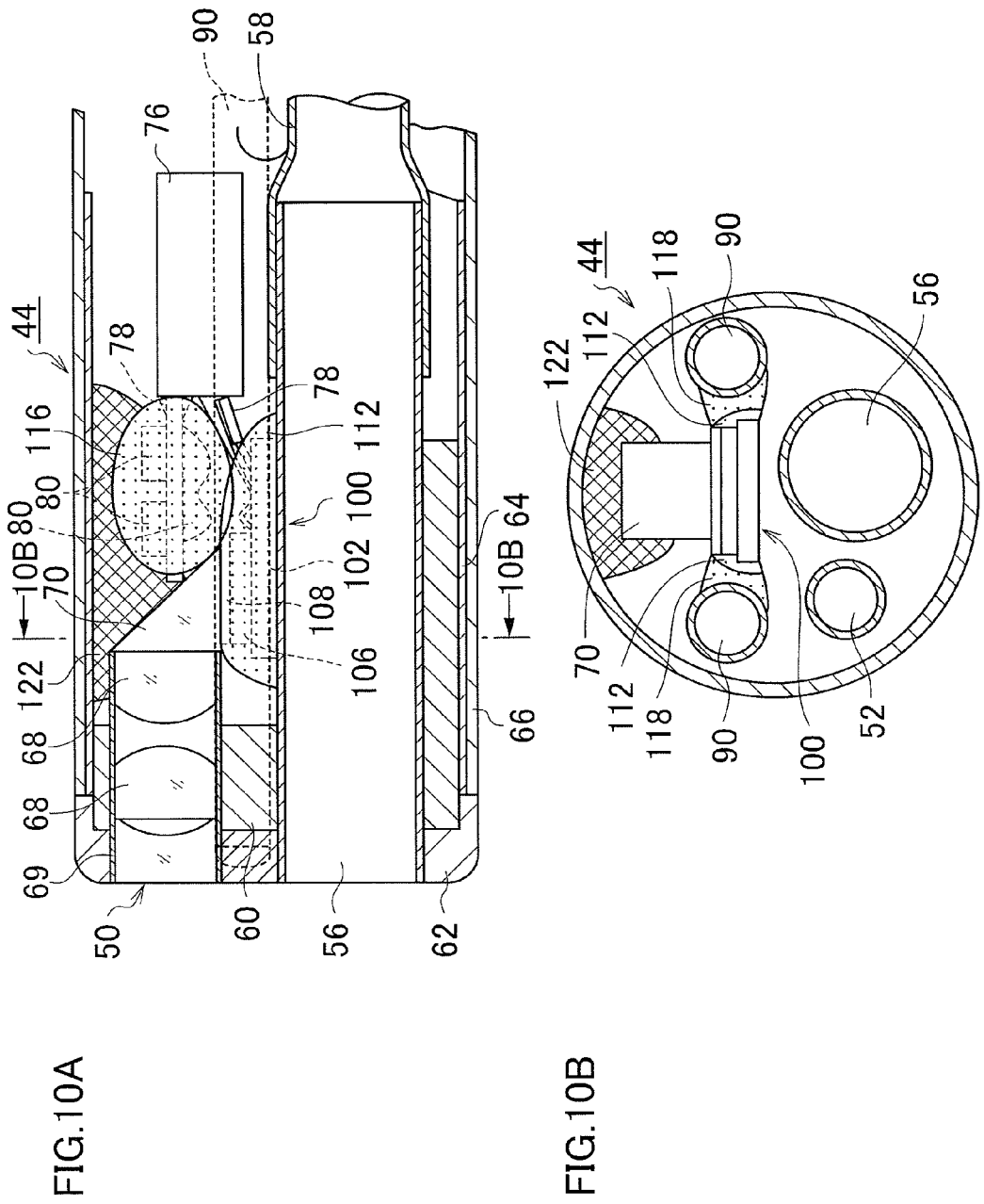
FIGS. 10A and 10B are sectional views of the distal end part of an endoscope insertion part in which an image pickup device is incorporated.

FIG. 10A illustrates a section of a distal end part 44 of an insertion part relating to a further embodiment of the presently disclosed subject matter. FIG. 10B is a sectional view based on the line 10B-10B. The configurations which are the same as those of the embodiment of FIG. 8 may be designated by the same reference numerals thereby omitting the description thereof. As illustrated in FIGS. 10A and 10B, the endoscope includes a heat release member 122 which thermally couples the circuit board 80 with the distal end sleeve 64. The heat release member 122 may be of any material having a high thermal conductivity, and a resin made up of a silicone, epoxy or urethane resin which has insulating properties and is incorporated with a diamond filler, or a graphite sheet can be used. This configuration can improve heat releasing capability.

What is claimed is:

1. An image pickup device, comprising:
   an image pickup element;
   a spacer surrounding a light receiving surface of the image pickup element;
   a cover glass attached to the spacer, the cover glass being disposed opposing to the light receiving surface; and
   an insulative resin configured to thermally couple the image pickup element with the cover glass, the insulative resin including a diamond filler, the insulative resin covers a side surface of the cover glass and a surface of the solid-state image pickup element.

2. The image pickup device according to claim 1, further comprising:
   a frame of graphite sheet configured to accommodate the image pickup element, the cover glass, and the insulative resin, the frame of graphite sheet being thermally coupled with the insulative resin.

3. An endoscope, comprising:
   the image pickup device according to claim 1;
   an image pickup optical system optically coupled with the image pickup device;
   a drive circuit electrically connected with the image pickup device;
   a light guide configured to radiate light from a illumination light source;
   a forceps opening;
   a tubular body configured to accommodate the image pickup device, the image pickup optical system, the drive circuit, the light guide, and the forceps opening; and
   a first insulative resin including a diamond filler the first insulative resin being adapted to thermally couple the image pickup device with the drive circuit.

4. The endoscope according to claim 3, further comprising:
   a second insulative resin including a diamond filler, the second insulative resin being adapted to thermally couple the image pickup device with the light guide.

5. The endoscope according to claim 3, wherein
   the frame of the graphite sheet accommodates the drive circuit and the first insulative resin.

6. The endoscope according to claim 3, wherein
   the insulative resin and the first insulative resin have a same composition.

7. The endoscope according to claim 4, wherein
   the first insulative resin and the second insulative resin have a same composition.

8. The endoscope according to claim 4, wherein
   the insulative resin, the first insulative resin and the second insulative resin have a same composition.

9. The endoscope according to claim 4, further comprising:
   a heat release member configured to thermally couple the forceps opening with any one of the insulative resin, the first insulative resin, and the second insulative resin.

* * * * *